(12) United States Patent
Yerushalmy

(10) Patent No.: US 6,638,241 B2
(45) Date of Patent: Oct. 28, 2003

(54) APPARATUS FOR TREATING BRUXISM

(76) Inventor: Israel Yerushalmy, 6 Kissufim Street, Tel Aviv 69355 (IL)

( * ) Notice: Subject to any disclaimer, the term of this patent is extended or adjusted under 35 U.S.C. 154(b) by 0 days.

(21) Appl. No.: 10/033,776

(22) Filed: Jan. 3, 2002

(65) Prior Publication Data

US 2003/0125661 A1 Jul. 3, 2003

(51) Int. Cl.[7] .................................................. A61M 1/00
(52) U.S. Cl. ........................... 604/31; 604/20; 604/503; 600/590
(58) Field of Search ................ 604/20, 31, 501, 604/503, 65–67, 21, 511; 600/27, 537, 546, 587, 590, 595, 26; 607/48, 62, 63, 72, 67

(56) References Cited

U.S. PATENT DOCUMENTS

| | | | | |
|---|---|---|---|---|
| 4,669,477 A | * | 6/1987 | Ober | 607/48 |
| 4,715,367 A | * | 12/1987 | Crossley | 600/27 |
| 5,213,568 A | * | 5/1993 | Lattin et al. | 604/20 |
| 6,149,577 A | * | 11/2000 | Bouldin et al. | 600/13 |

FOREIGN PATENT DOCUMENTS

WO  WO 200287681 A2 * 11/2002 .......... A61M/35/00

* cited by examiner

Primary Examiner—Brian L. Casler
Assistant Examiner—Lina R Kontos
(74) Attorney, Agent, or Firm—David Klein; Dekel Patent Ltd.

(57) ABSTRACT

Apparatus for the treatment of bruxism, including a biosensor adapted to sense a phenomenon associated with a bruxing event, and a relaxation stimulator in communication with the biosensor and adapted to provide a relaxation stimulus to relax at least one of an obruxism muscle and an obruxism nerve.

6 Claims, 1 Drawing Sheet

APPARATUS FOR TREATING BRUXISM

FIELD OF THE INVENTION

The present invention relates generally to apparatus for treating bruxism.

BACKGROUND OF THE INVENTION

Bruxism has generally been defined as nonfunctional clenching, grinding, gritting, gnashing, and/or clicking of the teeth. Bruxism may occur while a person is awake or asleep. When the phenomenon occurs during sleep, it is called nocturnal bruxism. Even when it occurs during waking hours, the bruxer is often not conscious of the activity. Biting force exerted during bruxism often significantly exceeds peak biting force exerted during normal chewing. Chronic bruxism may result in musculoskeletal pain, headaches, and damage to the teeth and/or the temporomandibular joint. Bruxism has been connected with temporomandibular disorders (TMD) or temporomandibular joint (TMJ) syndrome.

One of the known treatments in the prior art for nocturnal bruxism is the use of intra-oral occlusal splints or "mouth guards," which are generally semi-rigid plastic covers for the upper or lower teeth. Occlusal splints are generally fabricated for a specific individual from an impression taken of the individual's teeth. However, the occlusal splints often only protect the teeth themselves, while the user may still suffer musculoskeletal pain and possible damage to the temporomandibular joint. Moreover, occlusal splints present numerous inconveniences to the user. They may require frequent cleaning, may be difficult to clean, may require periodic replacement, may inhibit speech, and may be frequently lost.

Other techniques in the art attempt to combat bruxism through biofeedback. For example, an electromyograph has been used to sense the action of the masseter muscle. When muscle activity is detected, an audible tone is generated, which may alert the individual that he or she is bruxing. However, some biofeedback devices involve bulky electronics and may require electrodes to be attached adhesively to the face. Accordingly, such devices are considered impractical for long-term use in treating bruxism, and not well suited for consumer use.

Some variations on the biofeedback approach known in the art incorporate sensing means into an occlusal splint in order to sense the onset of bruxing. These approaches may require the presence of electrical devices in the mouth, including, in many cases, batteries, which may contain highly toxic substances. The electrical and chemical health risks of these devices add to the general drawbacks of intra-oral splints described above.

Another biofeedback device, called GRINDALERT is commercially available from Brux-Care, Inc., 84 Ship Street, Providence, R.I., USA (www.bruxcare.com). Instead of sensors in the mouth or bonded to the skin, GRINDALERT has a miniaturized sensing device incorporated into a headband. Bruxing may be sensed by the electrical activity of "obruxism muscles" (e.g., the temporalis and/or masseter muscles used to close the jaw). An electronics module processes the electrical signal from the bruxism muscles. When a threshold of intensity and duration is exceeded, the device emits an audible signal to provide feedback to the user, indicating the onset of a bruxing event. Data (including time, duration, and intensity) may be stored internally in response to a bruxing event. The data may be read out through connection to a personal computer, or via voice synthesis or a display.

However, a disadvantage of the audible devices of the art is that users may not wake up upon hearing the sound, especially if the user is a deep sleeper. In addition, users may become accustomed to the audible tone and unconsciously (or even consciously) ignore it.

SUMMARY OF THE INVENTION

The present invention seeks to provide improved apparatus for treatment of bruxism. The invention may use a variety of biosensors, such as but not limited to, electrodes, muscular activity sensors or nerve electrical impulse sensors, mounted in contact with a user's head, temples, forehead or jaw. In a preferred method of the invention, the biosensor provides biofeedback to a relaxation stimulant to relax the obruxism muscles or nerves, e.g., the temporalis and/or masseter muscles, or the maxillary or mandibular nerves associated with closing the jaw, such as but not limited to, the inferior alveolar nerve. The invention may relax the muscles or nerves by a variety of manners, such as but not limited to, chemical agents (e.g., laughing gas) or electrical stimulants to the muscles or nerves.

In contrast to the prior art, the invention may relax the bruxing event without any need for the patient to react to external, audible stimuli. Since the relaxing stimulus of the invention may work directly on the muscle or nerve, the patient may not become accustomed to the relaxing stimulus, thereby providing a significant improvement in reliability of the device.

There is thus provided in accordance with a preferred embodiment of the present invention apparatus for the treatment of bruxism, including a biosensor adapted to sense a phenomenon associated with a bruxing event, and a relaxation stimulator in communication with the biosensor and adapted to provide a relaxation stimulus to relax at least one of an obruxism muscle and an obruxism nerve.

In accordance with a preferred embodiment of the present invention the relaxation stimulator includes a drug delivery module adapted to administer a relaxant to a patient.

Further in accordance with a preferred embodiment of the present invention the drug delivery module includes an injection module adapted to inject a relaxant to a patient.

Still further in accordance with a preferred embodiment of the present invention the drug delivery module is adapted to emit a relaxant to air in a vicinity of a patient.

Further in accordance with a preferred embodiment of the present invention the drug delivery module includes a transdermal module adapted to administer a relaxant transdermally into a patient.

In accordance with a preferred embodiment of the present invention the drug delivery module includes a relaxant, such as a drug adapted to reduce transmission of nerve impulses to an obruxism muscle tissue.

Further in accordance with a preferred embodiment of the present invention the relaxation stimulator includes an electrical stimulator, such as a transcutaneous electrical stimulator.

In accordance with a preferred embodiment of the present invention the biosensor includes at least one of an electrode, a muscular activity sensor and a nerve electrical impulse sensor.

BRIEF DESCRIPTION OF THE DRAWINGS

The present invention will be understood and appreciated more fully from the following detailed description taken in conjunction with the drawings in which.

DETAILED DESCRIPTION OF PREFERRED EMBODIMENTS

Figure 1:
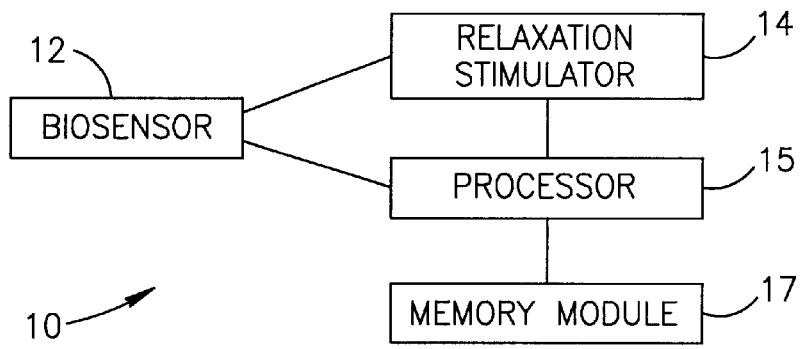
FIG. 1 is a simplified block diagram of apparatus for the treatment of bruxism, constructed and operative in accordance with a preferred embodiment of the present invention.

Reference is now made to FIG. 1, which illustrates in block diagram format, apparatus 10 for the treatment of bruxism, in accordance with a preferred embodiment of the present invention. Apparatus 10 preferably includes a biosensor 12 adapted to sense a phenomenon associated with a bruxing event. For example, biosensor 12 may comprise a pair of electrodes mounted in contact with a user's skull, for example near the temples. The voltage between the temple electrodes may be amplified and filtered to yield a signal indicative of the tension in the fibers of the temporalis muscle, and thus may indicate a bruxing event. As another example, biosensor 12 may comprise a muscular activity sensor or a nerve electrical impulse sensor, mounted or near the user's head, temples, forehead or jaw.

A relaxation stimulator 14 is preferably in communication with biosensor 12. The relaxation stimulator 14 may be in wired or wireless communication (e.g., BLUETOOTH) with biosensor 12. The relaxation stimulator 14 preferably provides a relaxation stimulus to relax an obruxism muscle and/or nerve. A processor 15 may be provided in communication with biosensor 12 and the relaxation stimulator 14 for processing signals received from biosensor 12 and for controlling operation of the relaxation stimulator 14. A memory module 17 may be provided for storing data, such as but not limited to, data related to bruxing events sensed by biosensor 12, for example. The processor 15 may be programmable to allow flexibility in providing an optimum treatment plan for the patient.

Figure 2A:
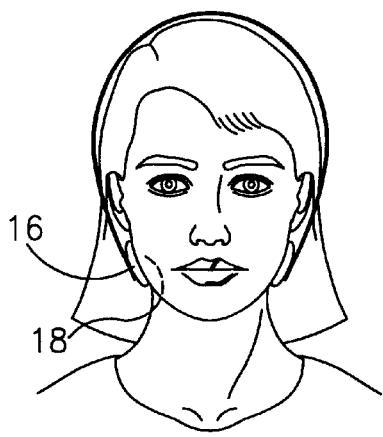
FIGS. 2A–2C are simplified illustrations of the apparatus of FIG. 1, in accordance with different preferred embodiments of the present invention, comprising a relaxation stimulator that comprises drug delivery modules.
Figure 2B:
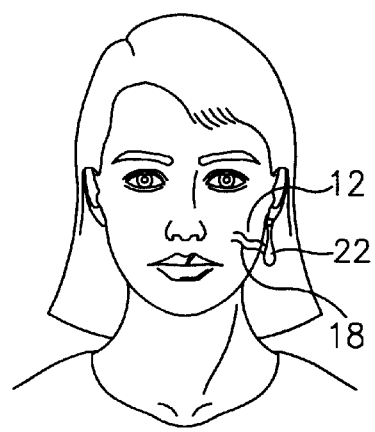
Figure 2C:
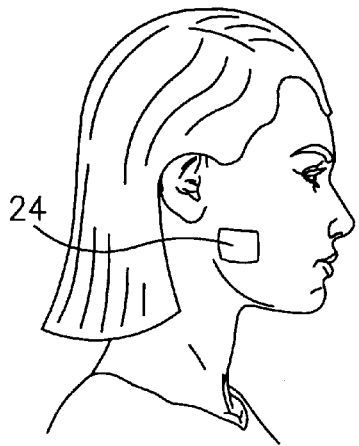

Reference is now made to FIGS. 2A–2C, which illustrate various embodiments of apparatus 10, wherein the relaxation stimulator 14 comprises a drug delivery module adapted to administer a relaxant to a patient. The relaxant may comprise a drug or chemical agent (the terms being used interchangeably) that reduces transmission of nerve impulses to an obruxism muscle tissue. Such drugs may include, but are not limited to, nitrous oxide (laughing gas) or diazepam (e.g., a benzodiazepine tranquilizer, such as VALIUM).

It is noted that in the present invention the term "relaxation" in all its inflections, refers not just to the state of obruxism muscles or other body tissues and parts becoming less tense, but also refers to arresting, reducing or otherwise preventing the bruxing forces applied by such muscles or other body tissues and parts. For example, in accordance with another embodiment of the present invention, the relaxant may comprise a drug or chemical agent that causes the obruxism muscles to "freeze", that is become somewhat motionless or fixed, so that the patient does not bite against his/her teeth, without necessarily reducing the tense state of the muscles. In another embodiment, the relaxant may reduce the biting force applied by the obruxism muscles without necessarily arresting the muscular activity or reducing the tension thereof. All of these influences on the obruxism muscles or nerves are included in the definition of "relaxation" in all its inflections throughout the specification and claims.

In FIG. 2A, the drug delivery module may comprise an injection module 16 adapted to inject a relaxant 18 to a patient by means of an injection needle 20. For purposes of example only, the injection module 16 may be worn as a headphone and relaxant 18 may be injected locally near the jaw of the patient or in other places as well.

In FIG. 2B, the drug delivery module may emit the relaxant 18 to air in the vicinity of the patient. For example, upon receiving a signal from biosensor 12, a microcapsule 22, containing the relaxant 18, may be ruptured to release the relaxant to the air. The drug delivery module including the microcapsule 22 may be worn as a pendant or earring, if desired.

In FIG. 2C, the drug delivery module may comprise a transdermal module 24, such as a skin patch, for example, which administers the relaxant 18 transdermally into the patient. Different techniques may be used to enhance the administration of the relaxant 18, such as but not limited to, iontophoresis.

Figure 3:
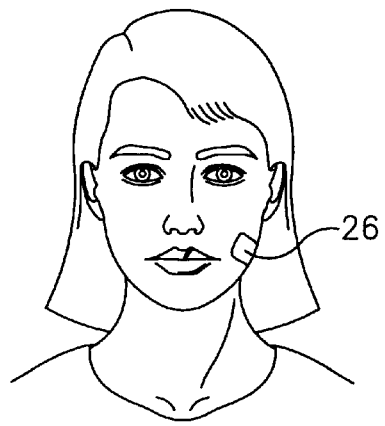
FIG. 3 is a simplified illustration of the apparatus of FIG. 1, in accordance with another preferred embodiment of the present invention, comprising a relaxation stimulator that comprises an electrical stimulator.

Reference is now made to FIG. 3, which illustrates another embodiment of apparatus 10, wherein the relaxation stimulator 14 comprises an electrical stimulator 26, such as a transcutaneous electrical stimulator. For example, upon receiving a signal from biosensor 12, the electrical stimulator may provide an electrical relaxation stimulus to an obruxism muscle or nerve, so as to cause the patient to relax and stop bruxing.

It will be appreciated by person skilled in the art that the present invention is not limited by what has been particularly shown and described herein above. Rather the scope of the present invention is defined only by the claims that follow:

What is claimed is:

1. Apparatus for the treatment of bruxism, comprising:
   a biosensor adapted to sense a phenomenon associated with a bruxing event;
   a drug delivery module in communication with said biosensor and adapted to administer a relaxant to a patient, said relaxant being capable of relaxing at least one of an obruxism muscle and an obruxism nerve, and
   a processor in communication with said biosensor and said drug delivery module for processing signals received from biosensor and for controlling operation of said drug delivery module, wherein in response to said phenomenon, said biosensor communicates a signal to said processor and said processor operates said drug delivery module to initiate administration of said relaxant.

2. Apparatus according to claim 1 wherein said drug delivery module comprises an injection module adapted to inject the relaxant to the patient.

3. Apparatus according to claim 1 wherein said drug delivery module is adapted to emit the relaxant to air in a vicinity of the patient.

4. Apparatus according to claim 1 wherein said drug delivery module comprises a transdermal module adapted to administer the relaxant transdermally into the patient.

5. Apparatus according to claim 1 wherein said drug delivery module comprises the relaxant.

6. Apparatus according to claim 5 wherein said relaxant comprises a drug adapted to reduce transmission of nerve impulses to an obruxism muscle tissue.

* * * * *